(12) United States Patent
Ebel et al.

(10) Patent No.: US 6,559,318 B1
(45) Date of Patent: May 6, 2003

(54) METHOD FOR PRODUCING (2S,4R,9S)-OCTAHYDRO-1H-INDOLE-2-CARBOXYLIC ACID AND INTERMEDIATE PRODUCTS THEREFOR

(75) Inventors: Klaus Ebel, Lampertheim (DE); Frank Ohlbach, Dossenheim (DE); Christoph Nübling, Hassloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/869,651

(22) PCT Filed: Dec. 21, 1999

(86) PCT No.: PCT/EP99/10159

§ 371 (c)(1), (2), (4) Date: Feb. 5, 2002

(87) PCT Pub. No.: WO00/40555

PCT Pub. Date: Jul. 13, 2000

(30) Foreign Application Priority Data

Jan. 7, 1999 (DE) .......................... 199 00 205

(51) Int. Cl.$^7$ ............................................ C07D 209/04

(52) U.S. Cl. ...................................................... 548/492

(58) Field of Search ........................... 562/418; 548/492

(56) References Cited

U.S. PATENT DOCUMENTS

| | | | |
|---|---|---|---|
| 4,691,022 A | 9/1987 | Henning | 548/408 |
| 4,933,361 A | 6/1990 | Urbach et al. | 514/419 |
| 5,008,400 A | 4/1991 | Urbach et al. | 548/452 |
| 5,101,039 A | 3/1992 | Urbach et al. | 548/452 |

FOREIGN PATENT DOCUMENTS

| | | |
|---|---|---|
| DE | 33 22 530 | 1/1985 |
| EP | 0 084 164 | 7/1983 |
| EP | 0 132 580 | 2/1985 |
| EP | 0 267 098 | 5/1988 |

OTHER PUBLICATIONS

Brion et al. "Stereoselective Synthesis of a trans–Octahydroindole Derivative, Precursor of Trandolapril (RU 44 570), an Inhibitor of Angiotensin Converting Enzyme" Tetrahedron Letters vol. 33, No. 34 (1992) pp. 4889–4892.

Yanovskaya et al. "Communication 11. Some Reactions of 3–Echoxyacrolein and 3,3–Diethoxypropionaldehyde" Bulletin of the Russian Academy of Sciences, Division of Chemical Science (1962) pp. 623–629.

Scvekhgeimer "Aliphatic nitro alcohols, Synthesis, chemical transformations and applications" Russian Chemical Review vol. 67 No. 1 (1998) pp. 35–68.

Ballini et al. "Chemoselective Synthesis of Funcationalzed Conjugated Nitroalkenes" J. Org. Chem. vol. 57 (1992) pp. 2160–2162.

Melton et al. "A New Method for the Dehydration of Nitro Alcohols" J. Org. Chem. vol. 40, No. 14, (1975) pp. 2138–2139.

Miyashita et al. "2–Nitropropene" Organic Synthesis vol. 60 pp. 100–103.

Shechter et al. "Reactions of 1–Choloro–3–nitro–2–butene and Sodium 2–Propanenitronate; 3–Methyl–4–(2–nitro–2–propyl)–isoxazoline Oxide" J. Org. Chem. Soc. vol. 76 (1954) pp. 2716–2720.

Sowden et al. "Carbohydrate C–Nitroalcohols: the Acetylated Nitroölefins" J. Org. Chem Soc. vol. 69 (1947) pp. 1048–1050.

(List continued on next page.)

Primary Examiner—Alan L. Rotman
Assistant Examiner—Golam M. M. Shameem
(74) Attorney, Agent, or Firm—Wood, Phillips, Katz, Clark & Mortimer

(57) ABSTRACT

Described is a process for the preparation of (2S, 4R, 9S)-octahydro-1H-indole-2-carboxylic acid, comprising a) reacting a compound of the formula I $$(R^1O)_2CH—CH_2—CH(OR^2)_2 \qquad\qquad I$$

wherein $R^1$ and $R^2$ may be the same or different and represent each a $C_{1-4}$-alkyl group, with water in the presence of an acidic catalyst, b) subjecting the obtained 3,3-dialkoxypropionaldehyde of formula II $$(R^2O)_2CH—CH_2—CHO \qquad\qquad II$$

to a Henry-reaction with nitromethane, c) subjecting the obtained 4,4-dialkoxy-1-nitro-4-butanol of formula III $$(R^1O)_2CH—CH_2—CHOH—CH_2—NO_2 \qquad\qquad III$$

to a dehydration d) converting the obtained nitroolefin IV with the aid of a Diels-Alder reaction into the corresponding trans-4-(2,2-dialkoxyethyl)-5-nitro-1-caclohexene V e) hydrogenating the obtained substance V into the corresponding trans-4-(2,2-dialkoxyethyl)-5-amino-1-cyclohexane VI f) subjecting the compound VI to a resolution of racemate and obtaining the (1S, 2R)-1-amino-2-(2,2-dialkoxyethyl)-cyclohexane VII in enantiomerically pure form by enzymatic racemate resolution, g) hydrolysing the obtained compound VII to the corresponding aldehyde VIII h) converting the obtained aldehyde into the corresponding nitrite IX by reaction with cyanide ions and i) saponifying this nitrile to the (2S, 4R, 9S)-octahydro-1H-indole-2-carboxylic acid.

1 Claim, No Drawings

OTHER PUBLICATIONS

Jurczak et al. "Formation of Quarternary Salts of Sterically Hindered Bis–Quinolizidine Monolactams under High Pressure" Synthesis (1983) p. 920.

Ballini et al. "Nitro–Ketones in Organic Synthesis: A New, Short Synthesis of Racemic trans–2–Methyl–1, 7–dioxaspiro[5.5]undecane, trans, trans—and trans, cis–2,8–Dimethyl–1,7–dioxaspirol[5.5]undecane by Henry Reaction" Liebigs Ann. Chem. (1994) pp. 1235–1237.

Ballini et al. "A New, Highly Efficient Synthesis of Conjugated Nitrocycloalkenes" Tetrahedron Letters vol. 35, No. 31 (1994) pp. 5731–5734.

Saika et al. "An Improved Synthesis of Conjugated Nitroolefins" Synthesis (1994) pp. 685–686.

Knochel et al. "Dehydratisierung von Nitroaldolen mit Dichclohexylcarbodiimid: Herstellung von Nitroolefinen unter milden Bedingungen" Synthesis (1982) pp. 1017–1018.

METHOD FOR PRODUCING (2S,4R,9S)-OCTAHYDRO-1H-INDOLE-2-CARBOXYLIC ACID AND INTERMEDIATE PRODUCTS THEREFOR

This application is a 371 of PCT/EP99/10159 Dec. 21, 1999.

The present invention relates to a process for the preparation of (2S, 4R, 9S)-octahydro-1H-indole-2-carboxylic acid and intermediates, which can be used during the process. (2S, 4R, 9S)-octahydro-1H-indole-2-carboxylic acid has the formula

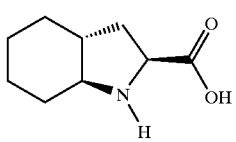

(2S, 4R, 9S)-octahydro-1H-indole-2-carboxylic acid is an important intermediate product for the manufacture of inhibitors for angiotensinase (DE 3322530, EP 267098). It is in particular a key product for the manufacture of Trandolapril (EP 84164).

The synthesis processes for (2S, 4R, 9S)-octahydro-1H-indole-2-carboxylic acid so far known in the art are very costly (DE 3322530, EP 267098). Now a simpler and cheaper process for the preparation of this substance has been found.

The present invention relates to a process for the preparation of (2S, 4R, 9S)-octahydro-1H-indole-2-carboxylic acid, consisting of the following steps a) reacting a compound of the formula I $(R^1O)_2CH-CH_2-CH(OR^2)_2$   I wherein $R^1$ and $R^2$ may be the same or different and represent each a $C_{1-4}$-alkyl group, with water in the presence of an acidic catalyst, b) subjecting the obtained 3,3-dialkoxypropionaldehyde of formula II $(R^1O)_2CH-CH_2-CHO$   II to a Henry-reaction with nitromethane, c) subjecting the obtained 4,4-dialkoxy-1-nitro-4-butanol of formula III $(R^1O)_2CH-CH_2-CHOH-CH_2-NO_2$   III to a dehydration d) converting the obtained nitroolefin IV with the aid of a Diels-Alder reaction into the corresponding trans-4-(2,2-dialkoxyethyl)-5-nitro-1-cyclohexene V

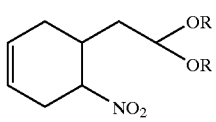

e) hydrogenating the obtained substance V into the corresponding trans-4-(2,2-dialkoxyethyl)-5-amino-1-cyclohexane VI

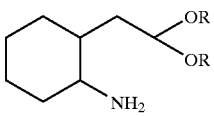

f) subjecting the compound VI to an racemate resolution and obtaining the (1S, 2R)-1-amino-2-(2,2-dialkoxyethyl)-cyclohexane VII,

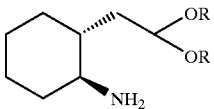

in enantiomerical pure form g) hydrolyzing the obtained compound VII to the corresponding aldehyde VIII

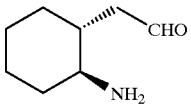

h) converting the obtained aldehyde into the corresponding nitrile IX by reaction with cyanide ions and

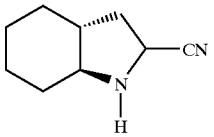

i) saponifying this nitrile to the (2S, 4R, 9S)-octahydro-1H-indole-2-carboxylic acid The hydrolysis of the 1,1,3,3-tetraalkoxyalkanes (I) to the corresponding 3,3-dialkoxypropionaldehydes (=malone dialdehyde monoacetales) (II) is effected by converting the educt with water with an acidic catalyst. As catalyst generally all catalysts known for the hydrolysis of acetates are usable. In particular suitable are strong protonic acids or strong acidic ion exchange materials, such as for example sulfuric acid, hydrochloric acid, phosphoric acid, toluenesulfonic acid, Nafion, ion exchange materials with sulfonic acid groups and the like.

Step b, the Henry reaction of the malone dialdehyde monoacetale with nitromethane to the 4,4-dialkoxy-1-nitrobutanol (III) is carried out under the usual conditions for this type of addition reaction (M.Shvekhgeimer, Russ.Chem.Rev. 67, 35–68 (1998)). As catalyst all catalysts described for those type of reaction can be envisaged, such as nitrogen containing bases, such as aliphatic amines or guanidine, basic ion exchange materials, Potassium fluoride, potassium fluoride supported on aluminium oxide, alkali or alkaline earth hydroxides or alkali or alkaline earth alcoholates, such as sodium methylate. Step b is carried out usually under basic conditions. As bases suitable are in particular tertiary amines, such as trimethylamine, triethylamine, tetramethylenediamine, tetramethyl-1,3-propanediamine, DBN and DABCO. The malone dialdehyde monoacetale can be employed as crude product, as obtained after hydrolysis, without any further purification.

In step c the 4,4-dialkoxy-1-nitro-2-butanol (III) is dehydrated to the 4,4-dialkoxy-1-nitro-2-butene (IV). For the dehydration all methods known for the dehydration of nitroalcoholes may be employed. The following are enumerated here: 1.direct dehydration with aluminium oxide (J.Org.Chem. 57, 2160–2162 (1992)), 2. Dehydration with methane sulfochloride and triethylamine (J.Org.Chem. 40, 2138–2139 (1975)) and 3. Dehydration using phthalic anhydride (Org.Synth. 60, 101 (1981)).

Dehydration c can also be effected by acylation of the alcohol with an acid anhydride and subsequent cleaving of the acid with bases, such as alkali carbonates or alkali hydrogen carbonates or nitrogen containing bases or aluminium oxide, see J.Am.Chem.Soc. 76, 2716 (1954), J.Am..Cem.Soc. 69, 1048 (1947), Synthesis 1983, 920, Liebigs Ann.Chem. 1994, 1235 and Tetrahedron Lett. 35, 5731 (1994). Further possibilities for dehydration are those using dicyclocarbodiimide with copper catalysis (Sythesis 1982, 1017) and those using triphenylphosphine/carbon tetrachloride/triethylamine (Synthesis 1994, 685).

In particular suitable for the dehydration c is the acylation of the nitroalcohol with acetanhydride and subsequent cleavage of acetic acid. Acetic acid is already partially cleaved off during acylation. Complete cleavage can be achieved thermally at temperatures of from 120 to 500° C. or with bases, such as alkali or alkaline earth carbonates, hydrogen carbonates or hydroxides of the aliphatic amines. For the acylation it is preferred to employ catalysts (for example 4-(dimethylamino)pyridine). During dehydration the thermodynamically more stable trans-product is formed mainly.

In step d the nitroolefin is reacted with butadiene in an Diels-Alder reaction. Pure thermal Diels-Alder reactions without catalysts are carried out at temperatures of from 50 to 200° C., preferably from 90 to 120° C., in aromatic hydrocarbons, such as benzene, toluene or xylene. With the use of catalysts the reaction temperature can be reduced. The trans-nitroolefin gives the trans-4-(2,2-dialkoxyethyl)-5-nitro-1-cyclohexene.

In step e the double bonds and the nitro group are hydrogenated. The hydrogenation may be effected in one step or in two steps. As catalysts all hydrogenation catalysts are suitable, preferably Raney nickel or Pd or Pt catalysts, such as Pd/C or Pt/C. The hydrogenation is carried out at from 20 to 150° C. As solvent suitable are alcoholes such ass methanol and ethanol or acetic acid.

The preparation of the enantiomerically pure form of (1S, 2R)-1-amino-2-(2,2-dialkoxyethyl)-cyclohexane (step f) can be effected by resolution of racemates in the usual manner. In particular suitable is the encymatic resolution of racemates. Therein the racemic mixture of (1S, 2R)— and (1R, 2S)-1-amino-2-(2,2-dialkoxyethyl)-cyclohexane is reacted with acylating agents, such as alkoxy acetic acid isopropyl ester, in the presence of hydrolases, in particular lipases. In this reaction the (1R, 2S)-enantiomer is acylatetd selectively while the desired (1S, 2R)-enantiomer does not react and can be separated from the reaction mixture by means of destination or chromatography. Suitable as lipase is in particular Novozym 435. Resolution occurs suitably at from 20 to 40° C.

The hydrolysis of the acetale (step g) to the aldehyde takes place suitably by boiling the acetate in an aqueous acid, such as hydrochloric acid, sulfuric acid or phosphoric acid.

The conversion of the aldehyde to the nitrile (step h) can be effected in particular by reaction with sodium cyanide under alkaline conditions, at a pH>9, wherein the nitrile is saponified directly into the sodium salt of the (2S, 4R, 9S)-octahydro-1H-indole-2-carboxylic acid (step i). The acid is obtaines by acidifying the reaction solution.

The present invention also relates to new compounds, used in the above described synthesis. These are the following:

2. 4,4-Dialkoxy-1-nitro-2-butenes of Formula IV

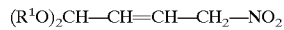

(R¹O)₂CH—CH=CH—CH₂—NO₂    IV 3. trans-4-(2,2-Dialkoxyethyl)-5-nitro-1-cyclohexenes of Formula V

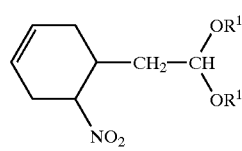

4. trans-4-(2,2-Dialkoxyethyl)-5-amino-1-cyclohexanes of Formula VI

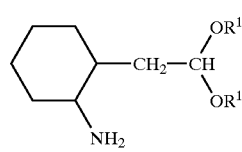

5. (1S, 2R)-1-amino-2-(2,2-dialkoxyethyl)-cyclohexanes of Formula VII

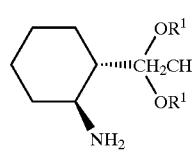

The aldehyde of formula VIII

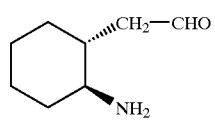

and the acid addition salts.

The new process for the preparation of (2S, 4R, 9S)-octahydro-1H-indole-2-carboxylic acid yields the substance in an higher yield, compared with the processes known so far for its preparation. Further the preparation is greatly simplified, since fewer process steps are needed. Finally the 1,1,3,3-tetraalkoxyalkanes, used as starting materials, are materials which can be prepared cost effective on an technical scale.

The new intermediates are key substances for the synthesis.

EXAMPLES

Example 1

Preparation of 3,3-dimethoxypropanale using an acidic ion exchange material as catalyst.

A mixture of 2756 g (16 mole) 95% 1,1,3,3-tetramethoxypropane, 292 g (16 mole ) water, 256 g (8 mole ) methanol and 20 g strong acidic ion exchange material (BayKat K 2431) is boiled under reflux for 1.5 hours in a 6 l stirring reactor made of stainless steel, Subsequently the mixture was cooled to 50° C. and the ion exchange material was filtered off. The filtrate obtained was adjusted to a pH of 2.5 and distilled over a column having 20 theoretical plates. The following fractions were obtained.

| Fraction No. | Pressure [mbar] | Temp. [° C.] | Amount [g] | Composition |
|---|---|---|---|---|
| 1 | 400–30 | 42–22 | 1200 | 87% methanol, 9% water |
| 2 | 20 | 30–51 | 84 | 56.2% DMPA |
| 3 | 20 | 51–57 | 575 | 98.9% DMPA |
| 4 | 20 | 57–69 | 349 | 68.6% DMPA, 31.0% TMP |
| 5 | 20 | 69–71 | 816 | 98.3% TMP |
| residue |  |  | 260 |  |

DMPA: dimethoxypropionaldehyde; TMP: tetramethoxypropane

Fraction 3 was employed for the next step. Fraction 4 was subjected to another distillation and the fraction distilling at from 51 to 57° C. (239 g) was added to fraction 3.

Of the 2756 g (16 mole) 95% tetramethoxypropane 925 g (5.6.mole) were recovered. This leads to the finding that 1831 g (10.4 mole) tetramethoxypropane were consumed, i.e. 65% of the employed tetramethoxypropane were converted. Fractions 3 and 4 contained together 575 g+237 g (=68.6% of 349 g)=812 g dimethoxypropionanldehyde. This corresponds to a yield of 66% on the basis of the tetramethoxypropane employed.

Example 2

4,4-Dimethoxy-1-nitro-2-butanol

A mixture of 122 g (2 mole) nitromethane and 122 g methanol were given and, under cooling to 20 to 30° C., 120.4 g (1 mole)+98% 3,3-dimethoxypropionanldehyde were added dropwise thereto. Then 52 g (0.25 mole) 45% aqueous solution of trimethylamine were added and stirring was conducted for additional 2 hours at 50° C. The easily volatile components were distilled off at a bottom temperature of at most 60° C. under vacuum (at the end 30 mbar). 181.5 g of an oil were obtained, containing 157.7 g (0.98 mole) 4,4-dimethoxy-1-nitro-butanol, as confirmed by GC. The crude product was, without further purification, employed in the next step. For the determination of the analytical data, a sample was distilled (Kugelrohr), after filtration over aluminium oxide:

$^1$H-NMR (CDCl$_3$) after distillation (Kugelrohr): δ (PPM)=1.62 (t, 2H, C—CH$_2$—C), 3.35 (s, 6H, O—CH$_3$), 3.84 (s, 1H, OH), 4.4–4.6 (m, 3H, CH—O and CH$_2$—NO$_2$), 4.62 (t, 1H, CH(OMe)$_2$)

Example 3 trans-4,4-Dimethoxy-1-nitro-1-butene

The crude product of the previous step (181 g) was dissolved in 360 ml ethyl acetate and 1.2 g (0.01 mole) 4-dimethylamino pyridine and 100.8 g (1.2 mole) solid sodium hydrogen carbonate were added. Subsequently 153 g (1.5 mole) acetic anhydrde were added dropwise. The temperature rose to 35° C. It was stirred for 2 hours at 50° C. Then 100 ml water were added to the reaction mixture, whereupon carbon dioxide evolved. After separation of the aqueous phase the organic phase was washed two times with 100 ml saturated sodium hydrogen carbonate solution and concentrated with a rotary evaporator. The residue was distilled at a wall temperature of 130° C. with a Sambay-evaporator at 4 mbar. 18 g of a residue were obtained and 151 orange-red distillate consisting of 68% 4,4-dimethoxy-1-nitro-1-butene, 10% 2-acetoxy-4,4-dimethoxy-1-nitro-1-butane, 1.5% 4,4-dimethoxy-1-nitro-2-butanol and 17% acetic acid. The distillate was dissolved in 300 ml ethyl acetate and washed two times with 100 ml saturated sodium hydrogen carbonate solution. The organic phase was separated, the ethyl acetate removed using a rotary evaporator and the residue distilled again. 128 g 4,4-dimethoxy-1-nitro-1-butene were obtained, with a purity of 80%, as confirmed by GC. This corresponds to a yield of 60%, calculated on the basis of 3,3-dimethoxypropionaldehyde.

The product obtained was used without further purification in the next step.

By distillation a sample with a purity 95% was obtained:

$^1$H-NMR (CDCl$_3$) δ=2.60 (t, 2H, C—CH$_2$—C), 3.35 (s, 6H, O—CH$_3$), 4.52 (t, 1H, CH(OMe)$_2$), 7.05–7.3 (m, 2H, olefin-H) Fine analysis of the olefin-protones revealed a ratio trans:cis of 14.2:1.

Example 4 trans-4-(2,2-Dimethoxyethyl)-5-nitro-1-cyclohexene 214 g (1.0 mole) 75% 4,4-dimethoxy-1-nitro-1-butene and 0.1 g phenothiazine were put in an autoclave at room temperature, together with 850 ml toluene. Then 216 g (4.0 mole) butadiene were added under pressure. Subsequently stirring was conducted under the own pressure (approx. 6 bar) for 30 hours at 100° C. The pressure was released and the temperature reduced. Finally toluene and unreacted butadiene were distilled off. 270 g of an oily residue were obtained, containing about 39% reaction product and about 10% educt, as confirmed by GC. The crude product was employed without any further purification in the next step.

By distillation (Kugelrohr) a sample having a GC-purity of 95% was obtained:

$^1$H-NMR (CDCl$_3$) δ (PPM)=1.5 (m, 1H), 1.7 (m, 1H), 1.9 (m, 1H), 2.35–2.75 (m, 4H), 3.30 (2s, 6H, O—CH$_3$), 4.5 (m, 2H, OCH(OMe)$_2$ and CHNO$_2$), 5.6–5.7 (m, 2H, olefin-H).

Example 5 trans-1-Amino-2-(2,2-dimethoxyethyl)-cyclohexane 270 g of the residue of the previous step were taken up in 540 ml methanol an filtered over sodium sulfate. subsequently hydrogenation was carried out with 21 g of 10% Pd/C as catalyst, for 10 hours at 150 bar hydrogen pressure at 100° C. The catalyst was filtered off, the residue was washed with 100 ml methanol and the filtrate was concentrated. The obtained residue was distilled over a Sambay-evaporator (6 mbar, 130° C.). 120 9 distillate were obtained, having a content of trans-1-amino-2-(2,2-dimethoxyethyl)-cyclohexane of 57%. The yield ove two steps, starting from 4,4-dimethoxy-1-nitro-1-butene was 36%.

The product could be crystallized as acetate by addition of acetic acid. For this reaction the crude amine was dissolved in diethyl ether, acetic acid was added (300 ml ether and 32 g acetic acid per 10 g amine) and the precipitated acetate was filtered of. Then the acetate was recrystallized from ethyl acetate. 1-amino-2-(2,2-dimethoxyethyl)-cyclohexane acetate with a melting point of from 92 to 94° C. was obtained. For the determination of the analytical data the free base was liberated from the acetate by addition of aqueous NaOH, followed by extraction with ethyl acetate, evaporation of the extract and distillation (Kugelrohr).

$^1$H-NMR (CDCl$_3$) δ (PPM)=0.9–1.4 (m, 8H), 1.6–1.9 (m, 4H), 1.98–2.1 (m, 1H)J, 2.1–2.2 (m, 1H), 3.36 (2s, 6H, O—CH$_3$), 4.50 (m, 1H, CH(OMe)$_2$)

Example 6

(1S, 2R)-1-amino-2-(2,2-Dimethoxyethyl)-cyclohexane

A dry solution of 2.1 g (11.2 mmole) trans-1-amino-2-(2,2-dimethoxyethyl)-cyclohexane and 1.38 g (10.4 mmole) methoxy acetic acid isopropyl ester in 20 ml MTBE was mixed with 200 mg immobilized lipase Novozym® 435 and shaken for 25 hours at room temperature. After this period of time the conversion was 49.5%. The (1R, 2S)-enantiomer was acylated to the methoxy acetamide, while the (1S, 2R)-enantiomer was not acylated. After removal of the enzyme by filtration, removal of the solvent using an rotary evaporator and purification by column chromatography (silica gel, eluation starting with MTSE and finally with MTBE/methanol) 970 mg of pure (1S, 2R)-1-amino-2-(2,2-dimethoxyethyl)-cyclohexane (46% yield) were obtained.

Example 7

(2S, 4R, 9S)-Octahydroindole-2-carboxylic Acid 2.25 g (0.01 mole) (1S, 2R)-1-amino-2-(2,2-dimethoxyethyl)-cyclohexane were refluxed in 50 ml 1N hydrochloric acid for 30 minutes. The solution was adjusted to a pH of 6–8 with aqueous NaOH. Then 0.7 g (0.015 mole) sodium cyanide were added and the pH was adjusted to 11 with aqueous NaOH. Heating under reflux was continued for another hour. The reaction solution was cooled, the pH was adjusted with hydrochloric acid to 6 and the product was extracted continuously with ethyl acetate. The extract was concentrated. 1.7 g of an oily residue were obtained, which was uniform as confirmed by TLC. The residue was dissolved in metylene chloride and the product was isolated as hydrochloride by introducing chlorine gas. The product corresponds to the hydrochloride prepared in accordance with example 1 of EP-A-267 098, Stade C.

What is claimed is:

1. Process for the preparation of (2S, 4R, 9S)-octahydro-1H-indole-2-carboxylic acid, comprising of the following steps
  a) reacting a compound of the formula I

  $$(R^1O)_2CH—CH_2—CH(OR^2)_2 \qquad I$$

wherein $R^1$ and $R^2$ may be the same or different and represent each a $C_{1-4}$-alkyl group, with water in the presence of an acidic catalyst,
  b) subjecting the obtained 3,3-dialkylpropionaldehyde of formula II

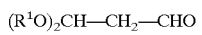
  $$(R^1O)_2CH—CH_2—CHO \qquad II$$

to a Henry-reaction with nitromethane,
  c) subjecting the obtained 4,4-dialkoxy-1-nitro-4-butanol of formula III

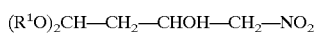
  $$(R^1O)_2CH—CH_2—CHOH—CH_2—NO_2 \qquad III$$

to a dehydration
  d) converting the obtained nitroolefin IV with the aid of a Diels-Alder reaction into the corresponding trans-4-(2,2-dialkoxyethyl)-5-nitro-1-cyclohexene V
  e) hydrogenating the obtained substance V into the corresponding trans-4-(2,2-dialkoxyethyl)-5-amino-1-cyclohexane VI
  f) subjecting the compound VI to a resolution of racemates and obtaining the (1S, 2R)-1-amino-2-(2,2-dialkoxyethyl)-cyclohexane VII in enantiomerically pure form
  g) hydrolysing the obtained compound VII to the corresponding aldehyde VIII
  H) converting the obtained aldehyde into the corresponding nitrile IX by reaction with cyanide ions

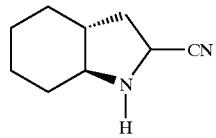

IX and
  i) saponifying this nitrile to the (2S, 4R, 9S)-octahydro-1H-indole-2-carboxylic acid.

* * * * *